US008536325B2

(12) United States Patent
Davis et al.

(10) Patent No.: US 8,536,325 B2
(45) Date of Patent: Sep. 17, 2013

(54) PROCESS FOR PURIFYING GUAR

(75) Inventors: James W. Davis, Argyle, TX (US); Howard Allen Ketelson, Dallas, TX (US); David L. Meadows, Colleyville, TX (US); John C. Baker, Fort Worth, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/396,305

(22) Filed: Feb. 14, 2012

(65) Prior Publication Data

US 2012/0142630 A1 Jun. 7, 2012

Related U.S. Application Data

(63) Continuation of application No. 12/701,339, filed on Feb. 5, 2010, now abandoned.

(60) Provisional application No. 61/150,215, filed on Feb. 5, 2009.

(51) Int. Cl.
*A61K 31/736* (2006.01)

(52) U.S. Cl.
USPC .......................................... 536/114

(58) Field of Classification Search
None
See application file for complete search history.

(56) References Cited

U.S. PATENT DOCUMENTS

| 3,042,668 | A | | 7/1962 | Monti et al. | |
|---|---|---|---|---|---|
| 4,218,327 | A | | 8/1980 | Wellington | |
| 4,447,336 | A | | 5/1984 | Vandersall | |
| 4,447,337 | A | | 5/1984 | Adl et al. | |
| 4,606,831 | A | | 8/1986 | Kegeler et al. | |
| 4,754,027 | A | | 6/1988 | Applegren | |
| 5,233,032 | A | | 8/1993 | Zody et al. | |
| 5,315,003 | A | | 5/1994 | Maruyama et al. | |
| 5,372,732 | A | * | 12/1994 | Harris et al. | 507/217 |
| 5,489,674 | A | | 2/1996 | Yeh et al. | |
| 5,536,825 | A | | 7/1996 | Yeh et al. | |
| 5,756,720 | A | | 5/1998 | Chowdhary | |
| 5,997,907 | A | | 12/1999 | Goswami et al. | |
| 6,063,402 | A | | 5/2000 | Gebert et al. | |
| 6,403,609 | B1 | | 6/2002 | Asgharian | |
| 6,664,381 | B1 | | 12/2003 | Wielinga | |
| 2003/0044479 | A1 | * | 3/2003 | Wielinga et al. | 424/776 |
| 2006/0027364 | A1 | | 2/2006 | Kelly et al. | |

FOREIGN PATENT DOCUMENTS

| EP | 0277499 | 8/1988 |
|---|---|---|
| EP | 0557627 | 9/1993 |
| EP | 0514890 | 9/1996 |
| EP | 0686643 | 6/2001 |
| EP | 0732342 | 8/2002 |
| EP | 0934343 | 1/2003 |
| EP | 1630176 | 7/2006 |
| EP | 0207045 | 2/2010 |
| JP | 55094901 | 7/1980 |
| JP | 63035606 | 2/1988 |
| JP | 63101402 | 6/1988 |
| JP | 01247049 | 2/1989 |
| JP | 05239105 | 9/1991 |
| JP | 05239106 | 9/1993 |
| WO | 97/11974 | 4/1997 |
| WO | 97/25354 | 7/1997 |
| WO | WO 99/06070 A1 * | 7/1998 |
| WO | 98/40108 | 9/1998 |
| WO | 03/008456 | 1/2003 |
| WO | 2006/017623 | 2/2006 |

OTHER PUBLICATIONS

Cheng et al., "Preparation and Characterization of Molecular Weight Fractions of Guar Galactomannans Using Acid and Enzymatic Hydrolysis," International Journal of Biological Macromolecules, vol. 31:29-35, 2002.
Feng et al., "Polyelectrolyte complex characterization with isothermal titration calorimetry and colloid titration", Colloids & Surfaces A: Physiochemical Eng Aspects, vol. 317:535-542, 2008.
Garcia et al., "Caracteristicas y Aplicaciones de la Goma Guar," Ciencia y Tecnologia Pharmaceutica, vol. 15(1):3-10, 2005.
Gebert et al., "Purified Guar Galactomannan as an Improved Pharmceutical Excipient," Pharmaceutical Development and Technology, vol. 3(3):315-323,1998.
Gittings et al., "The effect of solvent and ions on the structure and rheological properties of guar solutions", Journal Phys Chem A., vol. 105:9310-9315, 2001.
Kulkarni et al., "Rheological Properties of the Dispersions of Starch, Guar Gum, and Their Physical Mixtures in the Temperature Interval 298.15-333.15 K," Polym.-Plast. Technol. Eng., vol. 39(3):437-456, 2000.
Lapasin et al., "Rheology of Hydroxyethyl Guar Gum Derivatives," Carbohydrate Polymers, vol. 14:411-427, 1991.
Tantry et al., "Rheological Study of Guar Gum," Indian Journal of Pharmaceutical Sciences, pp. 74-76, 2001.
Venkataiah et al., "Rheological Properties of Hydroxypropyl- and Sodium Carboxymethyl-Substituted Guar Gums in Aqueous Solution," Journal of Applied Polymer Science, vol. 27:1533-1548, 1982.
Wientjes et al., "Linear Rheology of Guar Gum Solutions," Macromolecules, vol. 33:9594-9605, 2000.

* cited by examiner

*Primary Examiner* — Qiuwen Mi
(74) *Attorney, Agent, or Firm* — Mark E. Flanigan

(57) ABSTRACT

The present invention relates to processes for purifying guar comprising combining borate and guar in an aqueous solution and treating the aqueous solution with an organic solvent to induce precipitation of purified guar. Another embodiment of the present invention is directed to ophthalmic formulations comprising purified guar produced by the processes described.

7 Claims, 2 Drawing Sheets

PROCESS FOR PURIFYING GUAR

CROSS-REFERENCE TO RELATED APPLICATION

This application is a Continuation (CON) of U.S. application Ser. No. 12/701,339, now abandoned filed Feb. 5, 2010, priority of which is claimed under 35 U.S.C. §120, the contents of which are incorporated herein by reference. This application also claims priority under 35 U.S.C. §119 to U.S. Provisional Patent Application No. 61/150,215, filed Feb. 5, 2009, the entire contents of which are incorporated herein by reference.

TECHNICAL FIELD OF THE INVENTION

The present invention relates to guar and guar derivatives, and more particularly to processes for producing purified guar and guar derivatives.

BACKGROUND OF THE INVENTION

Guar gum is obtained from the endosperm of the guar (also known as clusterbean) plant *Cyamopsis tetragonoloba* (L.) Taub. Guar gum powder is typically produced by mechanically separating the endosperm (also known as guar "splits") from guar seed and hydrating the endosperm material in basic solution, followed by mechanical milling and drying to form the guar powder. U.S. Pat. No. 5,536,825 to Yeh et al. discloses techniques that may be used to form guar gum powder from guar splits.

Guar gum powder itself is comprised mostly of a water soluble, non-ionic polysaccharide consisting of a linear backbone chain of mannose linked together by $\beta$-(1-4) glycosidic linkage, and which forms branch points from the 6 position to galactose units through $\alpha$-(1-6) linkage. Processing techniques have been disclosed to improve or modify guar gum powder for food grade applications, drilling and hydraulic fracturing fluids, and other industrial applications. U.S. Pat. No. 4,754,027 to Applegren describes a technique for processing guar gum powder to produce an ingestible guar end product.

Many ophthalmic formulations comprise compounds that provide lubricity and other desirable properties. When these formulations are instilled in the eye, the properties of such compounds can prevent undesirable problems such as bioadhesion and the formation of friction-induced tissue damage, as well as encourage the natural healing and restoration of previously damaged tissues. Guar and guar derivatives such as hydroxypropyl guar (HP-guar) are used to provide characteristics such as lubricity to ophthalmic formulations.

Guar gum powder can be processed and purified by dissolving the powder in aqueous solution and adding organic solvents to induce precipitation. However, the precipitate thus formed often flocculates, forming a gum or viscous semi-solid having a fibrous character. Such precipitates tend to foul filtration and mixing equipment, making it difficult or impossible to utilize the guar material in a commercial-scale process for manufacturing aqueous pharmaceutical products, e.g., sterile ophthalmic solutions.

Prior approaches for addressing this problem have required that the resulting precipitate be mechanically milled or cut, either before or after a drying step, to render a dry solid. For example, EP 0514890 to Maruyama et al., discloses a method for purifying polysaccharides, including guar gum. The method of Maruyama requires the use of a precipitate cutter to generate the desired polysaccharide particle sizes for further processing and preferably uses isopropanol solution to induce precipitation. However, the dry solid thus rendered is of very low density, making it more expensive and inconvenient to ship and store in bulk quantities. In addition, this process has long processing and drying times due to the large amount of organics remaining after precipitation.

Previous disclosures have discussed the usefulness of guar and borate combinations for use in topical ophthalmic formulations, particularly gelling formulations. U.S. Pat. No. 6,403,609 to Asgharian describes such guar/borate combinations, but does not disclose a process for producing guar from guar gum powder.

BRIEF SUMMARY OF THE INVENTION

The present invention generally relates to processes for producing guar and guar derivatives. The materials produced via the processes of the present invention are particularly useful as components of aqueous ophthalmic pharmaceuticals products.

The present inventors have unexpectedly discovered that combining borate and guar in aqueous solution as part of a guar processing method yields a granular guar precipitate with improved purity, solubility, clarity, and thermal stability properties relative to guar produced by known processes. Guar produced by processes according to the present invention also has improved hydration characteristics.

Without being bound by theory, it appears that guar forms an anionic polyelectrolyte polymer with borate that can phase separate via salting out. This means that, in solution, if the charge of the polymer is adjusted with salts, buffers and/or pH then it can go from a solution to a highly crosslinked particle that can precipitate over time. Addition of any organic solvent will further induce the thus-formed precipitate to sediment from the supernatant. This discovery can be incorporated into scaleable manufacturing processes with few controlled process and rheological parameters. The guar thus produced has desirable viscosity and solution transmission properties, hydrates quickly in solution, and has an improved purity profile.

Embodiments of the present invention are directed to processes for manufacturing pharmaceutical grade guar compositions which comprise combining borate and guar in aqueous solution and precipitating guar by adding an organic solvent to the aqueous solution.

The present invention is further directed to processes for producing guar derivatives (e.g., hydroxyethyl guar and carboxymethylhydroxypropyl guar) that are particularly suitable for use in ophthalmic pharmaceutical compositions that are formulated for local administration.

The present invention is also directed to the provision of compositions produced by the described processes that are well-suited for pharmaceutical and medical applications, particularly as lubricants and viscosity enhancers.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention.

BRIEF DESCRIPTION OF THE DRAWINGS

A more complete understanding of the present invention and the advantages thereof may be acquired by referring to the following description, taken in conjunction with the figures of the accompanying drawing in which like reference numbers indicate like features and wherein.

DETAILED DESCRIPTION OF THE INVENTION

Figure 1:
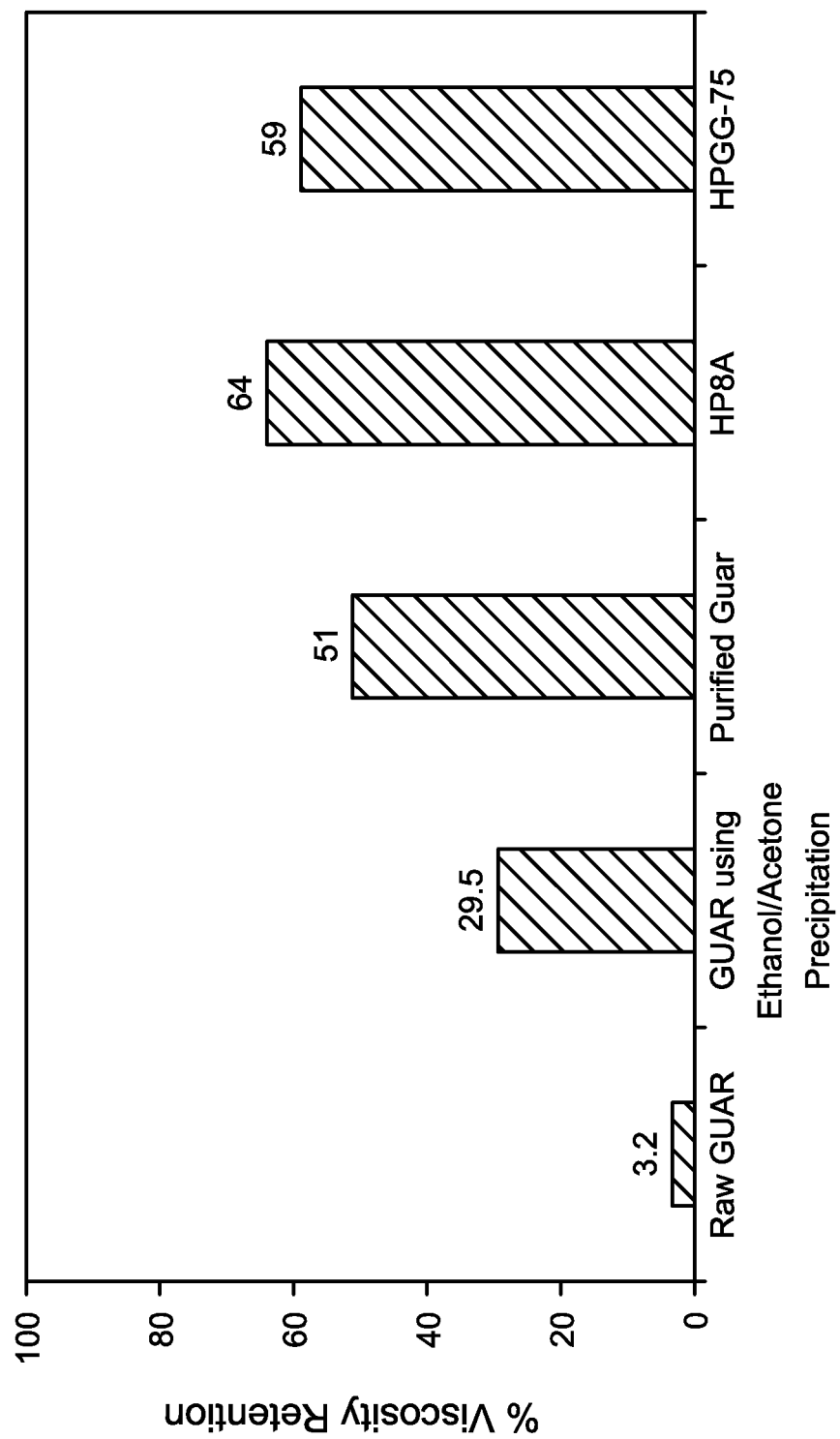
FIG. 1 is a bar graph comparing the measured stability of heat-sterilized guars.

Guar powder and water are combined to form an aqueous solution or slurry. The guar and water slurry is then mixed to disperse the guar. The guar concentration in water may vary, but is typically 0.1% to 1.5% w/v. In preferred embodiments, the guar is added in an amount sufficient to provide a final concentration of less than 1.0% w/v and preferably about 0.5% to 0.8% w/v and allowed to hydrate in the water for 2 hours or more at a pH of about 6.0 to 7.0. Different times and pH conditions for hydration may be used in other embodiments. Various temperatures may also be used for hydration. In one embodiment, hydration at 70° C. is preferred.

The aqueous guar solution is then combined with a borate source, optionally following one or more filtration steps prior to combination with borate. Following the addition of borate, an organic solvent is added to the borate and guar solution to induce precipitation of guar. The precipitated guar is then isolated, optionally with one or more precipitation and/or washing steps preceding the isolation. The isolated guar is dried and optionally milled to produce a desired particle size and homogeneity.

Guar gum and guar derivatives are generally available in powder form with various levels of purity. These powders are preferred for use in embodiments of the present invention. Guar derivatives that are commercially available include, but are not limited to, derivatives such as those containing hydroxyethyl, hydroxypropyl and carboxymethylhydroxypropyl substitutions, and other hydrophobic derivatives. Other guar derivatives used with embodiments of the present invention include cationic, anionic guar gums. Such guar and guar derivatives may be obtained, for example, from Rhodia, Inc. (Cranbury, N.J.), Hercules, Inc. (Wilmington, Del.), TIC Gum, Inc. (Belcamp, Md.), AEP Colloids, Inc. (Hadley, N.Y.), and Lamberti USA, Inc. (Hungerford, Tex.). A preferred guar gum powder is USP or general grade guar powder obtained from TIC Gum.

Borate sources used in embodiments of the present invention are boric acid and other borate salts such as sodium borate (borax) and potassium borate. Boric acid is preferred. Borate is typically added to a concentration of 0.05% to 0.5% w/v when combined with aqueous guar; 0.01% w/v is preferred. However, other concentrations may be used in processes of the present invention. Also, the concentration of borate may vary depending on pH, the concentration of guar in the aqueous guar solution, mixing time, etc. The use of alkyl borates (e.g., trimethyl borate) and phenyl borates may allow for the subsequent precipitation step to occur at higher pH.

The processes of the present invention comprise a precipitation step utilizing the addition of an organic solvent. In preferred embodiments, the organic solvent is added to the guar and borate solution to induce precipitation. Various organic solvents may be used, such as ethanol, acetone, and isopropanol; however, acetone is preferred. One or more organic solvents may be used, and the solvents may additionally be mixed with water in various ratios. For the initial guar precipitation, a 1:1 acetone and water solution is preferred, and the solution is added gradually to a final ratio of 1:1 with the guar and borate solution.

The optional filtration step preceding the combination of borate and guar may utilize various filters and filtration techniques known to those of skill in the art. A preferred filtration technique utilizes depth filters, such as the 40 µm, 20 µm and 10 µm SealKleen® filters produced by Pall Corp. (East Hills, N.Y.). Activated carbon filters such as the MilliStak™ series produced by Millipore (Billerica, Mass.) may also be used. Pressure and temperature control may be utilized during the filtration step depending on the filters and filter systems used.

The guar solid produced following the precipitation step(s) of the present invention may be isolated using filtration equipment known to those of skill in the art, such as 10 micron filter plates or filters readily available from companies such as Whatman, Inc. (Florham Park, N.J.). Other separation techniques such as centrifugation may also be used.

Once the precipitate resulting from the final precipitation and washing is separated by filtration or centrifugation or other separation techniques, the precipitate may be dried and optionally milled using available techniques for these procedures to generate a final purified guar powder.

The guar compositions produced by the processes of the present invention may be used in various types of products, but are particularly useful in pharmaceutical and medical products that function as lubricants and/or humectants. Such formulations may optionally comprise one or more additional excipients and/or one or more additional active ingredients.

Excipients commonly used in pharmaceutical formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the guar. In preferred embodiments, the excipients to be included in the formulations are typically selected on the basis of their inertness towards the guar component of the formulations.

Relative to ophthalmic formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68.

The formulations set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, amino alcohols such as AMP-95, or sorbic acid. In certain embodiments, the formulation may be self-preserved so that no preservation agent is required.

For ophthalmic administration, the formulation may be a solution, a suspension, or a gel. In preferred aspects, formulations that include the guar or guar derivative will be formulated for topical application to the eye in aqueous solution in the form of drops. The term "aqueous" typically denotes an aqueous formulation wherein the formulation is >50%, more preferably >75% and in particular >90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

In other aspects, components of the invention may be delivered to the eye as a concentrated gel or a similar vehicle, or as dissolvable inserts that are placed beneath the eyelids.

The formulations of the present invention that are adapted for topical administration to the eye are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The formulations of the present invention generally have an osmolality in the range of 220-320 mOsm/kg, and preferably have an osmolality in the range of 235-300 mOsm/kg. The ophthalmic formulations will generally be formulated as sterile aqueous solutions.

In certain embodiments, the guar compositions of the present invention are formulated with one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain formulations of the present invention may be used with contact lenses or other ophthalmic products.

It is also contemplated that the concentrations of the ingredients comprising the formulations of the present invention can vary. In preferred embodiments, the guar component is present in ophthalmic formulations at a concentration of about 0.1% to 0.25% w/v. However, the concentrations can vary depending on the addition, substitution, and/or subtraction of ingredients in a given formulation.

Preferred formulations are prepared using a buffering system that maintains the formulation at a pH of about 3 to a pH of about 8.0. Topical formulations (particularly topical ophthalmic formulations, as noted above) are preferred which have a physiological pH matching the tissue to which the formulation will be applied or dispensed.

In particular embodiments an ophthalmic formulation comprising a guar composition of the present invention is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations are administered at varying dosages, but typical dosages are one to two drops at each administration, or a comparable amount of a gel or other form of guar composition. One of ordinary skill in the art would be familiar with determining a therapeutic regimen for a specific indication.

The following examples are presented to further illustrate selected embodiments of the present invention.

EXAMPLE 1

A preferred process of the present invention utilizes USP grade guar powder obtained from TIC Gum, Inc. The raw guar powder is used to form a 0.8% aqueous guar solution. The solution is prepared by mixing guar (8 g) in water at a pH of 6-7 for 4 hrs. The aqueous guar solution is then pressure filtered (5 psi) at 25° C. through 40 μm pore size depth filters followed by 20 μm and 10 μm pore size depth filters (Pall SealKleen®). Boric acid (2 g) is then added to and dissolved in the filtered 0.8% guar solution. After dissolution of the boric acid, the pH is adjusted to 6-6.5 if necessary.

A guar precipitate is then formed from the guar and boric acid solution by titrating in acetone (10 mL/min) until precipitate starts to form while mixing. The mixing is stopped and the precipitate allowed to settle out for 30 min. Additional acetone is added and the resulting precipitate allowed to settle out for an additional 30 min. A total of 1 L of acetone was used for this quantity of guar and borate. Following the conclusion of the precipitation steps, the supernatant is decanted and the precipitate washed. A water:acetone solution (1:1; 1 L) is added to the precipitate and mixed for 1 hour. Following the wash, the supernatant is decanted. A second precipitation step is performed identically to that previously described. Following the second precipitation, a second wash step using 500 mL of acetone and 1 hour of mixing is performed. Precipitate is allowed to settle for 30 minutes and the supernatant is decanted.

Washed guar is then isolated by adding acetone (250 mL) and rinse and transfer with additional acetone to isolate guar in a Buchner funnel using filter paper (Whatman, Inc; Florham Park, N.J.). Isolated guar is then transferred to a drying plate and dried under vacuum (30 mmHg) at 60° C. for 24 hours.

EXAMPLE 2

TABLES 1 and 2 below show the result of an experiment comparing unprocessed guar (USP Grade; TIC Gum, Inc.) in aqueous solution compared to (i) guar purified using only ethanol/acetone precipitation and washing steps and (ii) guar purified using borate addition and ethanol/acetone. The 500 nm wavelength selected for transmission measurements is present in the visible spectrum region and corresponds to visual clarity of the solution, while the 280 nm wavelength is in the absorption region of protein impurities and is accordingly an indirect measurement of retained impurity.

As shown in TABLE 1, guar produced according to a process of the present invention ("Purified Guar") demonstrates better hydration characteristics compared to unpurified guar powder in aqueous solution ("Raw Guar") and guar purified using ethanol/acetone precipitation without the addition of borate. Purified Guar also shows superior transmission at 500 nm and 280 nm (TABLE 2), indicating much better visual clarity (500 nm) and a lower concentration of impurities (280 nm). Also, 0.5% aqueous solutions of Purified Guar did not produce precipitates after 4 weeks at room temperature, while other guars tested (raw guar, HP8A, and HPGG) all formed precipitates.

TABLE 1

0.5% Aqueous Guar Solutions at pH of 7 in DI water only and before autoclaving: Hydration Rate (% H)

| Formulation | % Hyd @ 2 hrs | % Hyd @ 4 hrs |
|---|---|---|
| Raw GUAR | 80.1 | 88.0 |
| GUAR Purified Using Only Ethanol/Acetone Precipitation | 65.9 | 93 |
| Purified Guar | 100 | 100 |

TABLE 2

0.5% Aqueous Guar Solutions at pH of 7 in DI water only and before autoclaving: Transmission (% T)

| Formulation | % T @ 500 nm | % T @ 280 nm |
|---|---|---|
| Raw GUAR | 47.5 | 6.8 |
| GUAR Purified Using Only Ethanol/Acetone Precipitation | 52.1 | 14.1 |
| Purified Guar | 92.5 | 73.7 |

TABLE 3

0.5% Aqueous Guar Solutions at pH of 7 in DI water only after autoclaving

| Formulation | Precipitate |
|---|---|
| Raw GUAR | ✓ |
| GUAR using Ethanol/Acetone Precipitation | ✓ |
| Purified Guar | |
| HP8A | ✓ |
| HPGG-75 | ✓ |

EXAMPLE 3

The thermal stability of guar produced according to the present invention was compared to that of unprocessed guar and guars processed using other techniques. In this experiment, guar samples were autoclaved for 35 minutes at 121° C. The results of the experiment are presented in FIG. 1.

As shown, raw guar and guar produced using an ethanol and acetone precipitation technique had poor thermal stability, with only 3.2% and 29.5% of pre-autoclave viscosity retained. Guar purified with a technique according to an embodiment of the present invention had viscosity retention comparable to that of commercially available HP8A guar and a hydroxypropylated guar derivative HPGG-75.

EXAMPLE 4

Figure 2:
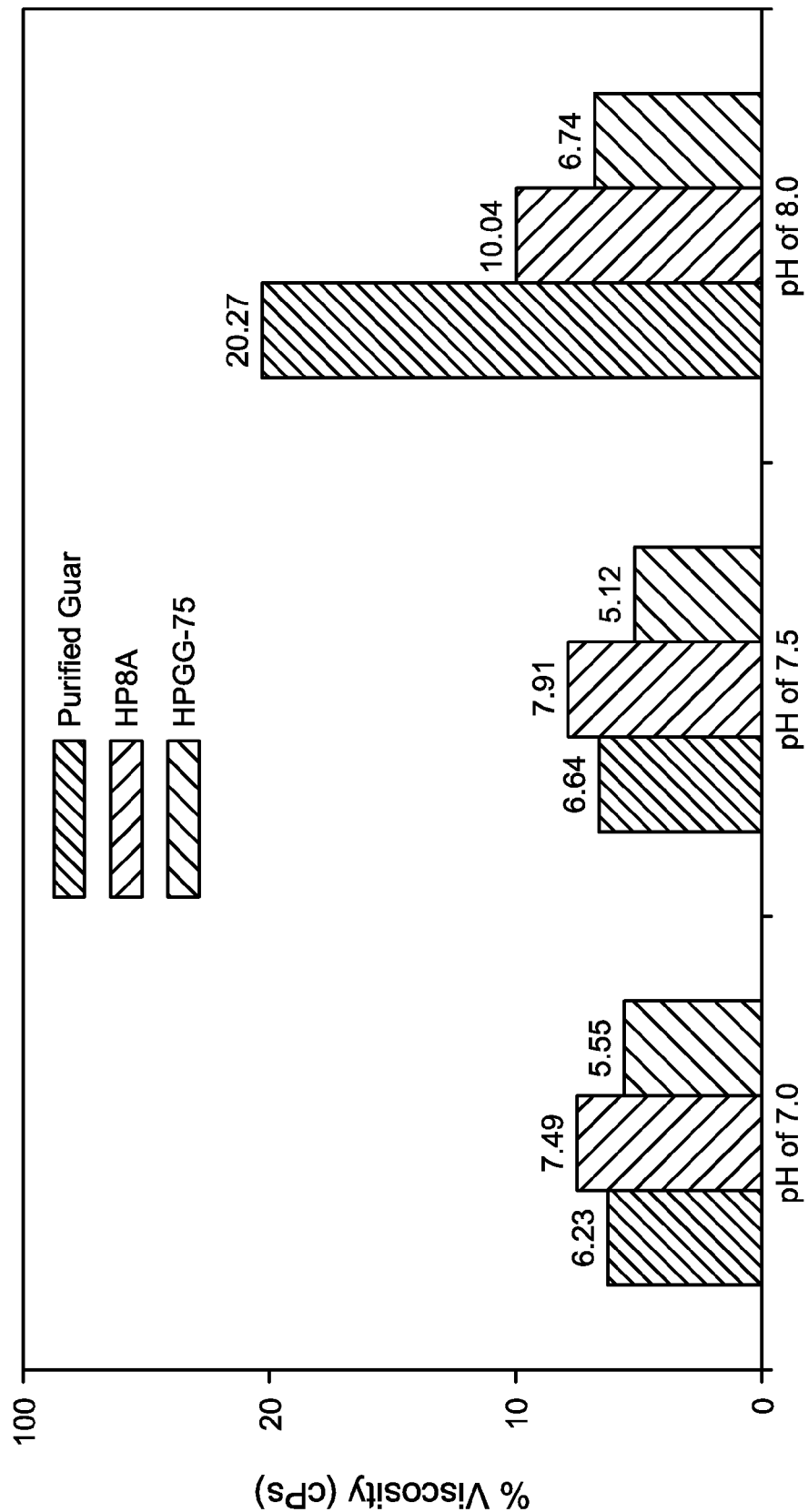
FIG. 2 is a bar graph comparing the measured viscosity of guar according to the present invention compared to hydroxypropylated guars processed using different techniques.

The pH sensitivity of a guar formulation according to an embodiment of the present invention was compared to that of commercially available HP8A guar and a hydroxypropylated guar derivative HPGG-75. The formulations comprised guar with boric acid, sodium chloride, sorbitol and polyquaternium-1. The viscosity was measured after one week at 40° C. As shown in FIG. 2, guar purified using the processes of the present invention showed good viscosity retention at physiological pH (7-8) and was significantly more sensitive to pH changes than was HP8A or HPGG-75, and demonstrates viscosity increases at pH 8.0.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the processes, compositions, and formulations described herein without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. A process for manufacturing guar comprising:
    combining borate and guar in an aqueous solution; and
    precipitating guar by adding an organic solvent to said aqueous solution; and wherein said organic solvent is acetone, said borate is added during said combining to form a concentration of 0.05% to 0.5% w/v in said aqueous solution, and said guar is added during said combining to form a concentration of less than 1.0% w/v in said aqueous solution wherein said acetone is added at a rate of 10 mL/minute to said aqueous solution.

2. A process according to claim 1 further comprising:
    filtering precipitated guar.

3. A process according to claim 2, wherein said filtering comprises filtering precipitated guar using one or more filters having a pore size of 40 μm or less.

4. A process according to claim 3, wherein said filters have a pore size selected from the group consisting of: 40 μm, 20 μm, and 10 μm.

5. A process according to claim 1 wherein said combining comprises adding borate to an aqueous guar solution.

6. A process according to claim 5 wherein said aqueous guar solution is filtered before said adding of borate.

7. A process according to claim 1 wherein said borate is selected from the group consisting of:
    sodium borate, potassium borate, boric acid, alkyl borates, trimethyl borate, phenyl borates, and combinations thereof.

* * * * *